(12) United States Patent
Ohta et al.

(10) Patent No.: US 10,729,723 B2
(45) Date of Patent: Aug. 4, 2020

(54) METHOD FOR INDUCING CELL REPROGRAMMING, AND METHOD FOR PRODUCING PLURIPOTENT CELLS

(71) Applicant: NATIONAL UNIVERSITY CORPORATION KUMAMOTO UNIVERSITY, Kumamoto-shi, Kumamoto (JP)

(72) Inventors: Kunimasa Ohta, Kumamoto (JP); Naofumi Ito, Kumamoto (JP)

(73) Assignee: NATIONAL UNIVERSITY CORPORATION KUMAMOTO UNIVERSITY, Kumamoto (JP)

(*) Notice: Subject to any disclaimer, the term of this patent is extended or adjusted under 35 U.S.C. 154(b) by 0 days.

(21) Appl. No.: 15/310,189

(22) PCT Filed: May 11, 2015

(86) PCT No.: PCT/JP2015/063457
§ 371 (c)(1),
(2) Date: Jul. 17, 2017

(87) PCT Pub. No.: WO2015/174364
PCT Pub. Date: Nov. 19, 2015

(65) Prior Publication Data
US 2017/0360833 A1     Dec. 21, 2017

(30) Foreign Application Priority Data
May 11, 2014  (JP) .................... 2014-098213

(51) Int. Cl.
| C12N 5/00 | (2006.01) |
| C12N 5/02 | (2006.01) |
| C12N 15/63 | (2006.01) |
| A61K 35/12 | (2015.01) |
| A61K 35/74 | (2015.01) |
| C12N 5/074 | (2010.01) |

(52) U.S. Cl.
CPC .............. *A61K 35/12* (2013.01); *A61K 35/74* (2013.01); *C12N 5/0696* (2013.01); *A61K 2035/122* (2013.01); *C12N 2500/72* (2013.01); *C12N 2506/00* (2013.01); *C12N 2506/1307* (2013.01); *C12N 2506/30* (2013.01)

(58) Field of Classification Search
CPC .. A61K 35/12; C12N 5/0696; C12N 2500/72; C12N 2506/00; C12N 2506/30; C12N 2506/1307
USPC ....................................... 435/377, 390, 455
See application file for complete search history.

(56) References Cited

U.S. PATENT DOCUMENTS

| 5,780,424 A | 7/1998 | Pineau et al. |
| 2002/0058293 A1 | 5/2002 | Takesako et al. |
| 2006/0222636 A1 | 10/2006 | Rambukkana |
| 2011/0318297 A1 | 12/2011 | Lu et al. |
| 2014/0255942 A1 | 9/2014 | Ohta |

FOREIGN PATENT DOCUMENTS

| EP | 0765667 B1 | 1/2001 |
| EP | 0970966 B1 | 2/2008 |
| JP | 9-124439 | 5/1997 |
| JP | 2005-512517 | 5/2005 |
| JP | 2012-519733 | 8/2012 |
| WO | 98/09990 | 3/1998 |
| WO | 9809990 | 3/1998 |
| WO | 2010104865 A2 | 9/2010 |
| WO | 2011008867 A1 | 1/2011 |
| WO | 2013/008803 | 1/2013 |
| WO | 2014/167943 | 10/2014 |
| WO | 2014167943 A1 | 10/2014 |

OTHER PUBLICATIONS

Timmerman, Benedikt, 2004, US 20040115210 A1.*
Li et al., 2014, Journal of Hematology & Oncology, 7:50, p. 1-18.*
Sommer et al., 2013, J. Cell. Physiol., vol. 228, p. 267-275.*
Zhang et al., 2012, Cell Cycle, vol. 11, No. 24, p. 1-9.*
Bryan et al., 2013, http://www.elsevierblogs.com/currentcomments/?p=962, Implications of protein fold switching, p. 1-4.*
Maqbool et al., 2015, Biochemical Society Transactions, vol. 43, No. 5, p. 1011-1017.*
International Search Report and Written Opinion, issued in International Patent Application No. PCT/JP2015/063457, dated Aug. 11, 2015.
Ohta K., "Lactic Acid Bacteria Convert Human Fibroblasts to Multipotent Cells," Journal of Japan Society for Lactic Acid Bacteria, Mar. 17, 2014, vol. 25, No. 1, pp. 13-17.
Matsubara A., "Studies on the Mechanisms for Action of Fibroblast Growth Factors in Stromel Cells of Hyperplastic Human Prostate," The Japanese Journal of Urology, 1995, vol. 86, No. 5, pp. 1034-1043.

(Continued)

*Primary Examiner* — Shin Lin Chen
(74) *Attorney, Agent, or Firm* — Hunton Andrews Kurth LLP

(57) ABSTRACT

An object of the present invention is to provide a pluripotent cell having high safety in application to regenerative medicine, and a method for production thereof. Another object of the present invention is to provide a pluripotent cell, particularly, having less concern for safety, such as a problem of cancerization of a cell, and the presence of bacteria in a cell, and a method for production thereof. According to the present invention, there is provided a method for producing a pluripotent cell from a somatic cell. The method comprises a step of inducing reprogramming of a somatic cell, by contacting the cell with a ribosome fraction derived from an organism. Further, according to the present invention, there is provided a composition for inducing reprogramming of a cell, comprising a ribosome fraction derived from an organism.

9 Claims, 11 Drawing Sheets

(56) References Cited

OTHER PUBLICATIONS

Masaki, T. et al., "Reprogramming Adult Schwann Cells to Stem Cell-Like Cells by Leprosy Bacilli Promotes Dissemination of Infection," Cell, 2013, vol. 152 No. 1-2, pp. 51-67.

Extended European Search Report dated Feb. 21, 2018 for European Patent application No. 15792267.5.

Masaki, Toshirio et al., "Reprogramming Adult Schwann Cells to Stem Cell-Like Cells by Leprosy Bacilli Promotes Dissenmination of Infection," Cell, vol. 152, No. 0, pp. 51-67, Jan. 17, 2013.

Takahashi, Kazutoshi et al., "Induction of Pluripotent Stem Cells from Adult Human Fibroblasts by Defined Factors," Cell, vol. 131, pp. 861-872, Nov. 30, 2007.

Ohta, Kunimasa et al., "Lactic Acid Bacteria Convert Human Fibroblasts to Multipotent Cells," PLos ONE, vol. 7, Issue 12, pp. 1-10, Dec. 2012.

\* cited by examiner

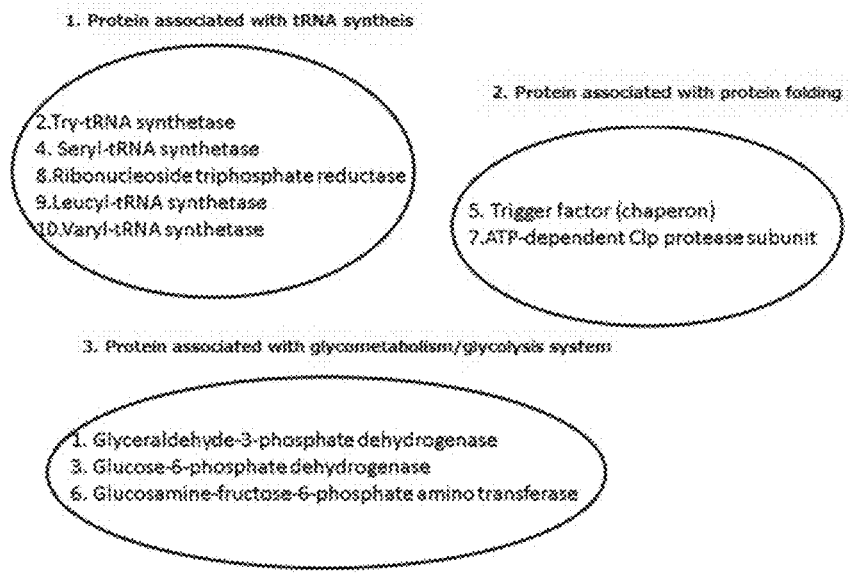
FIG. 3
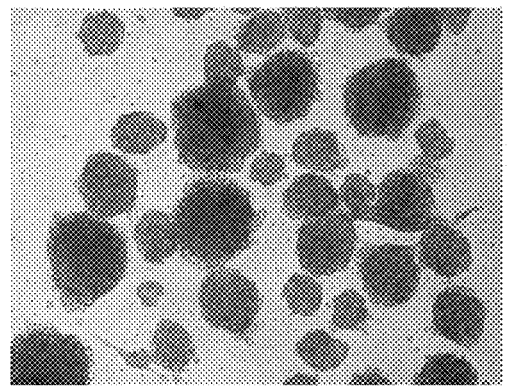
FIG. 4
Measurement of activity using purified 70S ribosome
| Sample | volume | Activity |
|---|---|---|
| 70S ribosome (precipitate) | 3.5 mg/50 µl | ++++ |
|  | 0.7 | ++ |
|  | 0.07 | + |
| Supernatant (fraction which was not precipitated by ultracentrifugation) | 3.5 | +++ |
|  | 0.7 | + |
|  | 0.07 | — |
FIG. 5

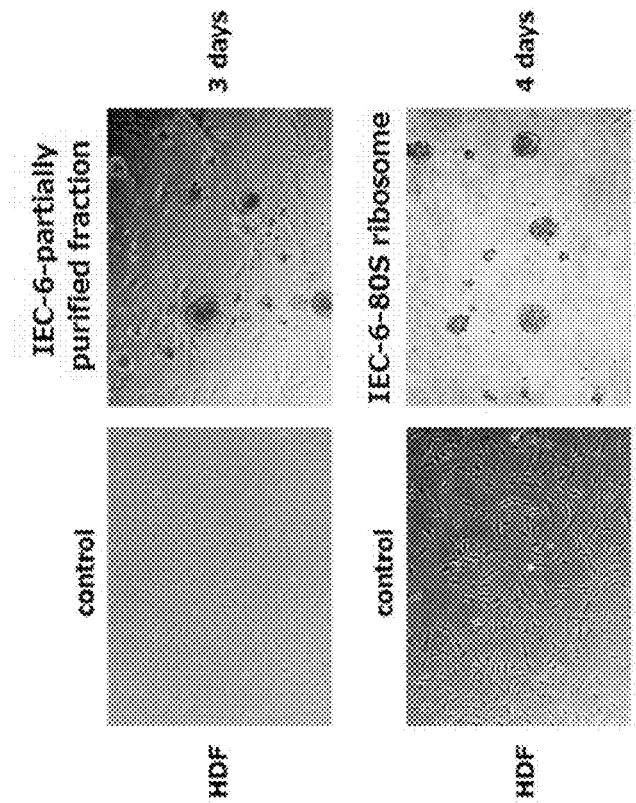

FIG. 13

| abbreviation | xxplanation | classification | classification | partially purified fraction | purified RBS |
|---|---|---|---|---|---|
| Lac | Lactobacillus (used in Example 1) | Prokaryote | Gram-positive | + | + |
| Lca | Lactobacillus | Prokaryote | Gram-positive | + | + |
| Lre | Lactobacillus | Prokaryote | Gram-positive | + | + |
| Sep | Staphylococcus related species | Prokaryote | Gram-positive | + | + |
| Bsu | Bacillus subtilis (Bacillus natto) | Prokaryote | Gram-positive | + | + |
| Eco | Escherichia coli | Prokaryote | Gram-negative | + | + |
| Ppu | Pseudomonas aeruginosa related species | Prokaryote | Gram-negative | + | + |
| Mlo | Rhizobia (plant mycorrhizal fungi) | Prokaryote | Gram-negative | + | + |
| Sce | Yeast | Eukaryote | | + | + |
| IEC-6 | Rat small intestine | Eukaryote | | + | + |

FIG. 14

METHOD FOR INDUCING CELL REPROGRAMMING, AND METHOD FOR PRODUCING PLURIPOTENT CELLS

CROSS REFERENCE TO RELATED APPLICATIONS

This application is a National Stage application from PCT/JP2015/063457 filed May 11, 2015, which claims Priority to Japanese Patent application 2014-098213 filed May 11, 2014.

FIELD OF THE INVENTION

The present invention relates to a method for inducing reprogramming of a cell. The present invention also relates to a method for producing a pluripotent/multipotent cell using such a method.

BACKGROUND OF THE INVENTION

An ES cell is called an embryonic stem cell, and was found from a mouse embryo in 1981 and from a human embryo in 1998. Research for constructing tissues or organs using the ES cell as a cell having the ability to change into a variety of kinds of cells other than cells constituting placenta (which is called as "pluripotency") has mainly been conducted. However, since the ES cell utilizes a fertilized egg which becomes a life when it grows smoothly, it has a major ethical problem. As another major problem, there is a problem of rejection. Even if differentiated cells or organs which were produced based on the ES cell are transplanted into a patient, there is a possibility that the immune system recognizes them as a nonself and attacks them.

In order to solve these problems of the ES cell, a group of Shinya Yamanaka Professor of Kyoto University developed a cell having the ability to change into a variety of kinds of cells from a skin cell which does not usually differentiate into a cell having other function, and named it as an iPS cells. It was shown that, when four factors called Yamanaka factors (Oct3/4, Sox2, Klf4, c-Myc) are introduced into a mouse or human skin cell using a retrovirus vector, initialization of the cell occurs, and a cell having pluripotency like the ES cell can be made [Non-Patent Document 1, and Non-Patent Document 2]. Since the cell used at this time is derived from a somatic cell such as a differentiated skin of a patient itself, when a cell differentiated from the iPS cells is transplanted into a patient, the immune system recognizes the organ as a self, and does not reject transplantation. By the finding of the iPS cells, two problems of "life ethics" and "rejection reaction" harbored by the ES cell have been cleared, however, the technique for standardizing the iPS cells is on the way of development and could not have completely overcome a problem of cancerization of a cell.

A process for producing a reprogrammed embryonic stem cell (ES)-like cell using a bacterium, *Mycobacterium leprae* or a component thereof has been proposed in Patent Document 1. Patent Document 1 describes a process for producing a reprogrammed ES-like cell by contacting and infecting an adult differentiated cell with a bacterium, *Mycobacterium leprae* itself, and a cell produced by this method, and describes that the bacterium which was contacted and infected exists in the produced ES-like cell. However, a bacterium, *Mycobacterium leprae* is a causation bacterium for leprosy *Bacillus*, and there is concern for safety in application to regenerative medicine.

Further, the present inventors have reported a process for producing a pluripotent cell from a somatic cell, by infecting the somatic cell with *Lactobacillus* or *Bacillus* natto which is a bacterium having the fermenting ability (Patent Document 2, Non-Patent Document 3). Still further, the present inventors have filed a patent application directed to a process for producing a pluripotent cell from a somatic cell, by using a crude extraction component from *Lactobacillus*, as PCT/JP2014/056948 (International Publication WO 2014/167943).

CITATION LIST

Patent Literature

[Patent Literature 1] US Patent Application Publication 2006/0222636
[Patent Literature 2] WO 2013/008803

Non Patent Literature

[Non Patent Literature 1] Takahashi and Yamanaka, Cell 126, 663-676, 2006.
[Non Patent Literature 2] Takahashi et al, Cell 131, 861-872, 2007
[Non Patent Literature 3] Ohta et al, PLoS ONE 7 (12): e51866, 2012

SUMMARY OF THE INVENTION

Problems to be Solved by the Invention

An object of the present invention is to provide a composition comprising a substance which induces reprogramming of a cell. Another object of the present invention is to provide a pluripotent/multipotent cell having high safety in application to regenerative medicine, and a process for production thereof.

Means to Solve the Problems

The present inventors have hitherto paid attention to a bacterium having the fermenting ability such as *Lactobacillus* and *Bacillus* natto, and examined a relationship between the bacterium having the fermenting ability and cells, and resultantly found out that when a human skin cell which finished cell differentiation is infected with *Lactobacillus* or *Bacillus* natto, respectively, this forms a cell-cluster like the ES cell and the iPS cells, and it is stained by an alkaline phosphatase staining. Further, the present inventors have found out that even a crude extraction component from *Lactobacillus* not from live *Lactobacillus* reprograms a human skin cell which finished cell differentiation, and can form a cell-cluster like the ES cell and the iPS cells.

Then, by specifying substances which induce reprogramming of a cell, the present inventors have found out that substances found not only in bacteria having the fermenting ability such as *Lactobacillus*, but also in many organisms induce reprogramming of a cell, leading to completion of the present invention. In addition, a cell-cluster which was induced from a human skin cell or a cancer cell using the substances was differentiation-induced into a variety of cells, and its differentiation into other cells was confirmed.

The present invention includes:

(1) A method for inducing reprogramming of a somatic cell or cancer cell, which is in vivo or isolated, of a mammal, comprising contacting the cell with a ribosome fraction derived from an organism.

(2) The method described in (1), wherein the somatic cell or the cancer cell is a cell derived from a human.

(3) The method described in (1) or (2), wherein the cell is an adherent cell.

(4) The method described in (3), further comprising a step of peeling the adherent cell from a cell support, before contact of the cell with the ribosome fraction.

(5) The method described in (4), wherein the step of peeling the cell is performed by trypsin treatment.

(6) The method described in any one of (1) to (5), wherein contact of the cell with the ribosome fraction is performed in the presence of methyl-β-cyclodextrin.

(7) The method described in any one of (1) to (6), wherein the ribosome fraction is a ribosome fraction derived from gram-negative bacteria.

(8) The method described in any one of (1) to (6), wherein the ribosome fraction is a ribosome fraction derived from gram-positive bacteria.

(9) The method described in any one of (1) to (6), wherein the ribosome fraction is a ribosome fraction derived from yeast.

(10) The method described in any one of (1) to (6), wherein the ribosome fraction is a ribosome fraction derived from a mammal.

(11) The method described in (7) or (8), wherein the ribosome fraction is a 30S ribosome fraction.

(12) The method described in (7) or (8), wherein the ribosome fraction is a 50S ribosome fraction.

(13) A pluripotent cell induced from a somatic cell or a cancer cell of a mammal, produced by the following steps:
a. contacting an isolated somatic cell or cancer cell with a ribosome fraction derived from an organism to culture or maintain the cell, and
b. recovering a formed cell-cluster.

(14) The pluripotent cell described in (13), wherein the somatic cell or the cancer cell is a cell derived from a human.

(15) The pluripotent cell described in (13) or (14), wherein the somatic cell is an adherent cell.

(16) The pluripotent cell described in (15), wherein a step of peeling the adherent cell from a cell support is further performed before the step (i).

(17) The pluripotent cell described in (16), wherein the step of peeling the cell is performed by trypsin treatment.

(18) The pluripotent cell described in any one of (13) to (17), wherein the step (i) is performed in the presence of methyl-β-cyclodextrin.

(19) The pluripotent cell described in any one of (13) to (18), wherein the ribosome fraction is a ribosome fraction derived from gram-negative bacteria.

(20) The pluripotent cell described in any one of (13) to (18), wherein the ribosome fraction is a ribosome fraction derived from gram-positive bacteria.

(21) The pluripotent cell described in any one of (13) to (18), wherein the ribosome fraction is a ribosome fraction derived from yeast.

(22) The pluripotent cell described in any one of (13) to (18), wherein the ribosome fraction is a ribosome fraction derived from a mammal.

(23) The pluripotent cell described in (19) or (20), wherein the ribosome fraction is a 30S ribosome fraction.

(24) The pluripotent cell described in (19) or (20), wherein the ribosome fraction is a 50S ribosome fraction.

(25) A pluripotent cell produced by using the method for inducing reprogramming of a cell described in any one of (1) to (12).

(26) A cell obtained by inducing differentiation of the pluripotent cell described in any one of (13) to (25) by culturing the cell in a differentiation inducing medium.

(27) The cell described in (26), wherein the cell is an adipocyte, an osteocyte, a chondrocyte, a nerve cell, a cardiac muscle cell, a liver cell, a pancreas cell, or a blood cell.

(28) A composition for inducing cell reprogramming, comprising a ribosome fraction derived from an organism.

(29) The composition described in (28), which is used for inducing reprogramming of a somatic cell or a cancer cell derived from a human.

(30) The composition according to (28) or (29), further comprising methyl-β-cyclodextrin.

(31) The composition described in any one of (28) to (30), wherein the ribosome fraction is a ribosome fraction derived from gram-negative bacteria.

(32) The composition described in any one of (28) to (30), wherein the ribosome fraction is a ribosome fraction derived from gram-positive bacteria.

(33) The composition described in any one of (28) to (30), wherein the ribosome fraction is a ribosome fraction derived from yeast.

(34) The composition described in any one of (28) to (30), wherein the ribosome fraction is a ribosome fraction derived from a mammal.

(35) The composition described in (31) or (32), wherein the ribosome fraction is a 30S ribosome fraction.

(36) The composition described in (31) or (32), wherein the ribosome fraction is a 50S ribosome fraction.

(37) An anti-cancer agent, comprising the composition described in any one of (28) to (36).

(38) A medium for producing a pluripotent cell from an isolated somatic cell or cancer cell derived from a mammal, comprising a ribosome fraction derived from an organism.

(39) The medium described in (38), further comprising methyl-β-cyclodextrin.

(40) A medium for producing a pluripotent cell from an isolated somatic cell or cancer cell derived from a mammal, comprising the composition described in any one of (28) to (36).

Effect of the Invention

In the present invention, a pluripotent cell can be produced from a somatic cell, without using introduction of genes into a somatic cell and forced expression. In the present invention, a pluripotent cell can be produced using a fraction of a ribosome (composed of a ribosomal RNA and a protein) which exists in all organisms from a prokaryote to a eukaryote or a composition comprising a component obtained therefrom.

BRIEF DESCRIPTION OF THE DRAWINGS

FIG. 3 is the result of grouping of proteins identified in Example 4.

FIG. 4 shows HDF cells which were cultured with a *Lactobacillus*-derived 70S ribosome fraction (after culturing for 7 days).

FIG. 5 is the result of confirmation of concentration dependency of the cell-cluster forming ability by a *Lactobacillus*-derived 70S ribosome fraction.

FIG. 12 shows the result of addition of a ribosome fraction, in trypsin treatment (Trypsinization), transfection, and no trypsin treatment (No treatment).

FIG. 13 shows the result of conformation of the cell-cluster forming ability, with a partially purified ribosome fraction and a purified 80S ribosome fraction derived from rat small intestine cells (IEC-6). An upper portion shows cells which were cultured in the presence of a partially purified ribosome fraction and a lower portion shows cells which were cultured in the presence of a 80S ribosome fraction (after culturing for 3 days). A left side is a control which was cultured without a ribosome fraction.

FIG. 14 shows the result of confirmation of the cell-cluster forming ability of a partially purified ribosome fraction, and a 70S or 80S purified ribosome fraction (Purified RBS), derived from various organisms.

MODE FOR CARRYING OUT THE INVENTION

Figure 1:
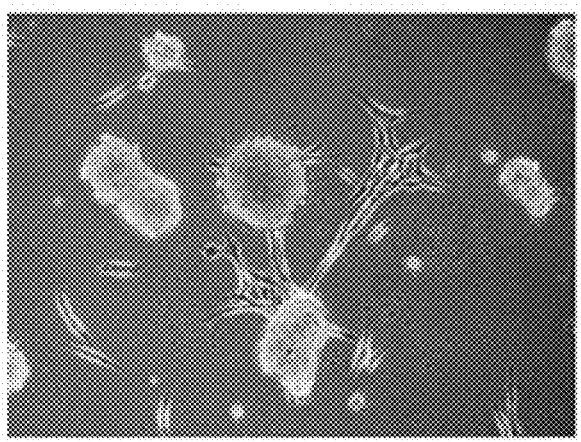
FIG. 1 shows HDF cells which were cultured with a *Lactobacillus* component prepared in Example 1 (after culturing for 3 days).

Hereinafter, the present invention will be described in detail with reference to the exemplary embodiments, along with the preferred methods and materials which can be used in practice of the present invention.

Unless otherwise specified in the sentences, any technical terms and scientific terms used in the present specification, have the same meaning as those generally understood by those of ordinary skill in the art to which the present invention belongs. Any materials and methods equivalent or similar to those described in the present specification can be used for practicing the present invention.

All publications and patents cited herein in connection with the present invention described herein are incorporated herein by reference, for example, as indicating methodology, materials, etc. that can be used in the present invention.

In the present invention, "induces reprogramming of a cell" refers to transformation of the cell into a pluripotent/multipotent cell having the ability to differentiate into a variety of cells, like the ES cell and the iPS cells, by contacting a somatic cell or a cancer cell of a mammal, for example, an epithelial cell with a ribosome fraction derived from an organism or an component contained in the fraction. Herein, the contact means that a cell is brought into the state where the cell can contact with a ribosome fraction or an component contained in the fraction (hereinafter, unless otherwise indicated, or unless one of them is clearly meant from a context, both are collectively referred to as a ribosome fraction), and an aspect thereof is not particularly limited, but preferably, refers to that by existence of a ribosome fraction in the environment in which a somatic cell lives (e.g. medium), it can act on the somatic cell.

In contact of the ribosome fraction with the somatic cell of a mammal, the cell can also be pre-treated. For example, when an adherent somatic cell is used, it is preferable that the somatic cell is pre-treated, and the cell is peeled from a support for the cell (e.g. a culturing dish or a cell culturing support) in advance.

Examples of pre-treatment of the cell before contact with the ribosome fraction include, for example, digestive enzyme treatment, specifically, trypsin treatment, or treatment with a commercially available cell peeling liquid, for example, a non-enzymatic cell peeling liquid, and trypsin treatment is preferable.

In the present invention, a living body from which a "ribosome fraction" is derived may be either of from a prokaryote to a eukaryote. A ribosome is not greatly different in a structure itself in all organisms, from a textbook's point of view, and is composed of a rRNA and a protein, and it is stated that a rRNA is involved in an active center of a catalytic reaction, and a protein is involved in structural stabilization of a ribosome. As the function, a ribosome is responsible for synthesis of proteins, and in a prokaryote, 30S (small subunit) makes a tRNA bind to a mRNA, and 50S (large subunit) has a role in a peptide formation (in a eukaryote, 40S and 60S, respectively).

Examples of the prokaryote from which the ribosome fraction used in the present invention is derived include Gram-positive bacteria and Gram-negative bacteria. Examples of the Gram-positive bacteria include, for example, Lactobacillus, Staphylococcus, Staphylococcus related species, Bacillus subtilis (Bacillus natto) and the like. Examples of representative Lactobacillus include lactobacilli belonging to genus Lactobacillus, genus Bifidobacterium, genus Enterococcus, genus Lactococcus, genus Pediococcus, genus Leuconostoc, genus Streptococcus etc. Examples of the Gram-negative bacteria include, for example, Escherichia coli, Pseudomonas aeruginosa related species, and rhizobia (plant mycorrhizal fungi).

Examples of the eukaryote from which the ribosome fraction used in the present invention is derived are not limited to, but include fungi, and animal species. Examples of the fungi include yeast, mushroom, and mold. Animal species may be either of an invertebrate or a vertebrate, and examples of the vertebrate include a mammal. When animal species are used, the "ribosome fraction derived from a living body" of the present invention may be a ribosome fraction derived from any organ, tissue or cell of an animal.

The "ribosome fraction" used in the present invention may be a partially purified fraction or a purified fraction of a ribosome, and further, may be either of a small subunit fraction (30S in a prokaryote, 40S in a eukaryote), or a large subunit fraction (50S in a prokaryote, 60S in a eukaryote). Furthermore, it is also possible to subject any fraction of them to arbitrary treatment, and extract or separate a part of components which induce reprogramming of a cell, and they are also included in the "ribosome fraction" of the present invention. That is, any fraction prepared from a partially purified fraction of a ribosome prepared from an organism is included in the ribosome fraction of the present invention, as far as it has the cell-cluster forming ability. For example, the partially purified fraction of a ribosome is suspended in a buffer, and further, (ultra) centrifugation can be performed to fractionate the suspension into a purified fraction (precipitate) of a ribosome and the supernatant. Preferable in the present invention is the purified fraction of a ribosome, but in such a case, under the separation condition used, a ribosome is also contained in the supernatant, and as a result, when a fraction of the supernatant also has the cell-cluster forming ability, it is also included in the ribosome fraction of the present invention. In addition, a purified ribosome fraction, for example, a purified 70S ribosome fraction can be separated into a 30S ribosome fraction and a 50S ribosome fraction by gradient (e.g. sucrose gradient) ultracentrifugation, and both are included in the ribosome fraction of the present invention.

The "ribosome fraction" used in the present invention is preferably a fraction in which a rRNA is contained in the state where a high order structure thereof is maintained.

A "composition for inducing cell reprograming" in the present invention comprises any of the aforementioned ribosome fractions derived from an organism.

A kind of the somatic cell used for inducing reprogramming or producing the pluripotent cell in the present invention is not particularly limited, but any somatic cell can be used. That is, the somatic cell mentioned in the present invention includes all cells other than a reproductive cell among cells constituting a living body, and may be a differentiated somatic cell, or an undifferentiated stem cell, differentiation of which has partially progressed. Examples thereof are not limited to, but include differentiated cells such as an epithelial cell, an endothelial cell, a fibroblast cell (skin cell etc.), an intestine cell, a liver cell, a spleen cell, a pancreas cell, a kidney cell, a hair cell, a muscle cell, a brain cell, a lung cell, a fat cell, and a stomach mucosa cell, and somatic stem cells, differentiation of which has partially progressed, such as a neural stem cell, a hematopoietic stem cell, a mesenchymal stem cell, and a dental pulp stem cell, and a tissue precursor cell. These cells are generally classified as an adherent cell. An origin of the somatic cell is not particularly limited, as far as it is a mammal, but is preferably a rodent such as a mouse, or a primate such as a human, and particularly preferably a human or a mouse. Additionally, when a human somatic cell is used, a somatic cell of any of a fetus, a neonate or an adult may be used. When the pluripotent cell produced by the method of the present invention is used in treatment of a disease such as regenerative medicine, it is preferable to use a somatic cell separated from a patient itself suffering from the disease. Alternatively, in the present invention, as a cell, a cancer cell can be used. A non-cancerous cell can be produced from a cancer cell, by contacting the cancer cell with the ribosome fraction. In the present invention, a step of contacting the somatic cell or the cancer cell with the ribosome fraction can be performed in vitro or in vivo.

The pluripotent cell mentioned in the present invention refers to a cell having the self-replicating ability under the predetermined culturing condition, and having the ability to differentiate pluripotentially/multipotentially into many kinds of cells (ectodermal cell, mesodermal cell, endodermal cell, etc.) under the predetermined differentiation-inducing condition (such a cell is also called a stem cell).

The pluripotent cell which was induced by the method of the present invention has the self-replicating ability under the predetermined culturing condition, but has the characteristic that it does not have the infinite proliferating ability like iPS cells.

The pluripotent cell which was induced by the method of the present invention also has the characteristic that there is no difference from an own cell, and a risk of cancerization is not increased by impartation of pluripotency.

When the pluripotent cell is produced by contacting the somatic cell with the ribosome fraction in accordance with the present invention, a cell-cluster forming efficiency can be enhanced by contacting the somatic cell with the ribosome fraction, in the presence of methyl-β-cyclodextrin.

In the present invention, the pluripotent cell or the non-cancerous cell (cell which was made non-cancerous by reprogramming a cancer cell) can be produced or cultured, by culturing the somatic cell in the presence of the ribosome fraction, using a normal medium for cell culturing. Such a medium is not particularly limited, but any medium which can be used for culturing the ES cell or the iPS cells can be used, and examples thereof are not limited to, but include Dulbecco's Modified Eagle Medium (DMEM), Eagle Minimum Essential Medium (EMEM), Iscove's Modified Dulbecco's Medium (IMDM), Alpha-Minimum Essential Medium (α-MEM), RPMI 1640, Ham-F-12, MCDB, and modified media thereof. As the medium, from a view point of subsequent use of the produced pluripotent cell and an induction efficiency, a serum-free medium is preferable, and further, if necessary, various growth factors, cytokines, hormones, for example, components involved in proliferation/maintenance of a human ES cell, such as FGF-2, TGFβ-1, activin A, Noggin, BDNF, NGF, NT-1, NT-2, and NT-3 may be added. Such a medium comprising the ribosome fraction is also a part of the present invention. Additionally, the differentiating ability and the proliferating ability of the separated pluripotent cell can be confirmed by utilizing confirmation means which are known regarding the ES cell.

Intended use of the pluripotent cell and the non-cancerous cell which are produced by the method of the present invention is not particularly limited, but those cells can be used in various tests/researches and treatment of diseases. For example, by treating the pluripotent cell obtained by the method of the present invention with retinoic acid, a growth factor such as EGF, or glucocorticoid, a desired differentiated cell (e.g. nerve cell, cardiac muscle cell, liver cell, pancreas cell, blood cell etc.) can be induced, and stem cell therapy by autologous cell transplantation can be attained by returning the thus obtained differentiated cell to a patient.

Examples of a central nervous disease which can be treated using the pluripotent cell of the present invention include Parkinson's disease, Alzheimer's disease, multiple sclerosis, cerebral infarction, and spinal cord injury. For treating Parkinson's disease, the pluripotent cell is differentiated into a dopaminergic neuron, and can be transplanted into corpus striatum of a Parkinson's disease patient. Differentiation into a dopaminergic neuron can be progressed, for example, by co-culturing a PA6 cell which is a mouse stromal cell strain and the pluripotent cell of the present invention under the serum-free condition. In treatment of Alzheimer's disease, cerebral infarction and spinal cord injury, the pluripotent cell of the present invention is differentiation-induced into a nerve stem cell, and thereafter, can be transplanted into a damaged site.

The pluripotent cell of the present invention can also be used in treatment of hepatic diseases such as hepatitis, cirrhosis hepatitis, and liver failure. In order to treat these diseases, the pluripotent cell of the present invention is differentiated into a liver cell or a liver stem cell, and can be transplanted. By culturing the pluripotent cell of the present invention for 5 days in the presence of activin A, and thereafter, culturing the cell with hepatocyte growth factor (HGF) for about 1 week, a liver cell or a liver stem cell can be obtained.

Further, the pluripotent cell of the present invention can be used for treating a pancreatic disease such as type I diabetes. In the case of type I diabetes, the pluripotent cell of the present invention is differentiated into a pancreatic β cell, and can be transplanted into pancreas. A method for differentiating the pluripotent cell of the present invention into a pancreatic β cell can be conducted in accordance with a method of differentiating the ES cell into a pancreatic β cell.

Further, the pluripotent cell of the present invention can be used in treating heart failure associated with an ischemic heart disease. For treating heart failure, it is preferable that the pluripotent cell of the present invention is differentiated into a cardiac muscle cell, and thereafter, transplanted into a damaged site. By adding Noggin to a medium from 3 days before formation of embryoid body, a cardiac muscle cell can be obtained from the pluripotent cell of the present invention, in about 2 weeks after formation of embryoid body.

Additionally, according to the present invention, a non-cancerous cell can be produced from a cancer cell, by contacting the cancer cell with the ribosome fraction. Accordingly, a composition comprising the ribosome fraction used in the present invention is useful as an anti-cancer agent.

Further, since the ribosome fraction provided by the present invention can reprogram a differentiated cell and a cell which caused abnormal differentiation such as a cancer cell, it can be used as an additive for medicaments or cosmetics.

The present invention will be specifically illustrated by way of the following Examples, but the present invention is not limited by the following Examples.

EXAMPLES

Example 1: Preparation of a *Lactobacillus* Component

*Lactobacillus* was purchased from Institute of Physical and Chemical Research (RIKEN), BioResource Center, Japan Collection of Microorganisms. After a MRS medium was sterilized with high pressure steam, *Lactobacillus* (*Lactobacillus acidophilus*; JCM1021: hereinafter, referred to as Lac) was inoculated into 20 ml of a MRS medium, and shaking-cultured at 37° C. for 2 to 3 days. Then, cells were inoculated into a 3 L shaking flask containing 1 L of the sterilized medium, and shaking-cultured at 37° C. for 3 to 4 days. Bacterial cells were collected from 1 L of the resulting culturing liquid by centrifugation at 10,000 rpm for 10 minutes. The cells were suspended in PBS, washed by repeating centrifugation three times, and suspended in 30 ml of PBS (pH 7.0). The cell suspension was homogenized for 30 minutes with OUTPUT 3, Duty 50% on an ice, in a Branson sonicator 250D ultrasound homogenizer (Branson). To the resulting cell extract was added 3.42 g of ammonium sulfate (ammonium sulfate concentration 20%), the mixture was cooled at 4° C. for 2 hours, and the cell residues were removed by centrifugation at 8,000 rpm and 4° C. for 10 minutes. After the supernatant was recovered, 8.28 g of ammonium sulfate was added, and the mixture was cooled in a refrigerator overnight. The sample was centrifuged at 10,000 rpm at 4° C. for 20 minutes to precipitate a protein fraction which precipitates at 20 to 60% saturation of the ammonium sulfate concentration. The precipitate was dissolved in 5 ml of a 0.02M Triethanolamine (TEA) buffer (pH 7.5) (total amount is around 7.5 ml), the solution was placed into a dialysis membrane (Thermo slide A dialyzer pore size 20,000 MW), and dialyzed against 0.02M TEA buffer (pH 7.5) at 4° C. overnight to remove low-molecular substances. Then, the dialyzed sample was recovered, and filtered with a 100 kDa ultrafiltration filter (Millipore) to recover the concentrated sample which had not passed through the membrane. The protein fraction was quantitated using the Protein Assay Kit (Bio Rad), and was used in the following experiment as a "*Lactobacillus* component". The protein concentration was 5 mg/ml.

Example 2: Culturing of HDF Cells in the Presence of a *Lactobacillus* Component HDF cells (Human Dermal Fibroblasts, CELL APPLICATIONS, INC. Cat No. 106-05a) were cultured in the Fibroblast Growth Medium (CELL APPLICATION INC.) in a 10 cm dish. Cells were washed with 10 ml of CMF ($Ca^{2+}$ $Mg^{2+}$ free buffer), and 1 ml of a 0.25% trypsin solution (containing 1 mM EDTA) was added over an entire region. The cells were placed in a $CO_2$ incubator (37° C.) for 5 minutes, 3 ml of a trypsin inhibiting solution (CELL APPLICATION INC.) was added to suspend the cells, and the cell number was counted. The Lac-derived *Lactobacillus* component (20 µl per well) obtained in Example 1 was placed into a 24-well plate in advance, and $1\times10^5$ HDF cells were added. The cells were cultured in a 5% $CO_2$ incubator at 34° C.

As a result, a cell-cluster could be observed after several days. The result is shown in FIG. 1. Using this cell-cluster formation assay as an index, a fraction having the ability to form a cell-cluster, which had been separated by column chromatography used in the following experiment, was determined.

Example 3: Purification by Chromatography

The concentrated *Lactobacillus* component (50 µl, protein amount 0.25 mg) obtained in Example 1 was further separated by anion exchange chromatography (Hi Prep Q FF 16/10 column (GE Health Care)). A column (16 ml) equilibrated with a 0.02M TEA buffer (pH 7.5) was loaded with the *Lactobacillus* component, and elution was performed with 0 to 1M linear gradient of sodium chloride, to recover each fraction. Concerning the resulting fractions, the cell-cluster forming ability was confirmed, as in Example 2.

Then, the fraction for which the cell-cluster forming ability had been confirmed, was applied to gel filtration chromatography (Hi Load Superdex 200 prep grade (GE Health Care)) (20 mM TEA 0.15M NaCl), the cell-cluster forming ability of each fraction was measured as in Example 2, and the fractions having the activity were recovered.

The resulting active fractions were further eluted by ion exchange chromatography (RESOURCE Q (GE Health Care)) with 0 to 1M linear gradient of sodium chloride, each fraction was recovered, and the cell-cluster forming ability of each fraction was measured. Fractions for which the activity had been confirmed, were used as a chromatography-purified fraction.

Example 4: SDS-PAGE and MALDI-TOF-MS Analysis

Figure 2:
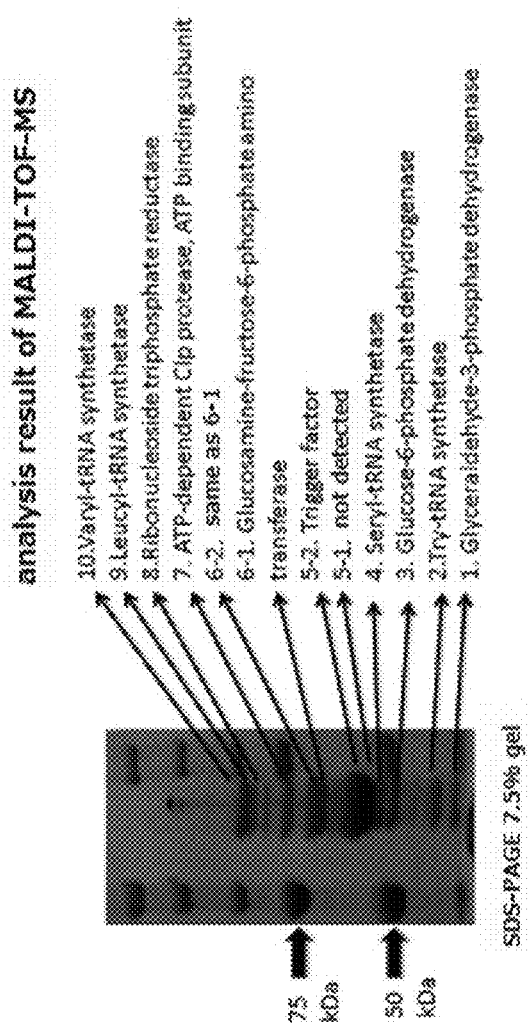
FIG. 2 shows the result when an active fraction which was obtained by purification by 3-step chromatography in Example 3 was separated by SDS-PAGE, and the result when each band was subjected to MALDI-TOF-MS analysis and proteins were identified.

The active fractions obtained by 3-step column chromatography (anion exchange chromatography-gel filtration chromatography-ion exchange chromatography) in Example 3 were separated by SDS-PAGE (7.5% gel). Ten bands were excised from the gel, digestion in the gel was performed, amino acid sequence analysis was performed using MALDI-TOF-MS (Bruker REFLEX™ MALDI-TOF MS), and proteins were identified using database retrieval. The result is shown in FIG. 2.

The resulting proteins were roughly grouped into the following three groups: Group 1: gene group associated with tRNA synthesis, Group 2: gene group associated with protein folding, Group 3: gene group associated with glycometabolism, and glycolysis system. The result of the grouping is shown in FIG. 3.

Example 5: Overexpression of Proteins

Among the determined proteins, proteins (7th ClpE and 5th to 2nd Trigger factor) which are molecules of 30 to 100 kDa (molecules which cannot pass through a 100 kDa ultrafiltration membrane, including a dimer etc.), and exist only in microorganisms were cloned, and overexpressed to produce His-tag proteins. Concerning the proteins, the cell-cluster forming ability was measured, but the activity was not found.

Example 6: Preparation of a *Lactobacillus* Ribosome and the Cell-Cluster Forming Ability The groups which were found out by analysis in Example 4 are molecules which are frequently detected upon purification of a ribosome. Additionally, in the case of a 30S subunit of *Escherichia coli*, since a ribosome is about 900 kDa, it cannot pass through a 100 kDa ultrafiltration membrane. On the other hand, a ribosome protein was not detected by MALDI-TOF-MS analysis, but since individual ribosome proteins are 15 kDa or less, it is considered that the ribosome proteins ran off to the outside of a gel in electrophoresis. Then, from *Lactobacillus* (Lac), a ribosome was prepared as shown below, and the cell-cluster forming ability was measured, as in Example 2.

(Material)

TMA-I buffer (10 mM Tris-HCl, pH 7.8, 30 mM $NH_4Cl$, 10 mM $MgCl_2$, 6 mM 2-mercaptoethanol)

Suc30-TMA-I (30% sucrose in TMA-I buffer)

(Preparation Step)

The followings were performed at 4° C. as much as possible.

1) Collected (2.5 g to 3.9 g per 1 L) bacterium cells were suspended in 40 ml of a TMA-I buffer, and after sonication (GTC 1 hour, output 4, duty 50%), it was confirmed with a microscope that cells were destructed.

2) Centrifugation was performed at 8,000 rpm for 5 minutes to recover the supernatant.

3) The supernatant was passed through a 0.45 µm filter.

4) Centrifugation was performed at 4° C. and 42,000 rpm for 30 minutes to recover the supernatant.

5) Centrifugation was performed at 4° C. and 36,000 rpm for 6 hours, and the supernatant was discarded. The precipitate was dissolved in 500 µl of a TMA-I buffer (partially purified ribosome fraction).

6) On 3.5 ml of Suc30-TMA-I was overlaid 500 µl of a partially purified ribosome solution.

7) Centrifugation was performed at 4° C. and 36,000 rpm for 15 hours, and the supernatant was discarded.

8) The precipitate was dissolved in 2 ml of a TMA-I buffer, and stored at −70° C. (purified 70S ribosome fraction).

(Result)

Using the purified 70S ribosome fraction obtained as described above, the cell-cluster forming ability was measured as in Example 2, and as a result, a cell-cluster was formed. The result is shown in FIG. 4.

Example 7: Concentration Dependency of the Cell-Cluster Forming Ability

Using the purified 70S ribosome fraction obtained in Example 6, whether a cell-cluster is formed concentration-dependently or not was studied. The result is shown in FIG.

5. As shown in FIG. 5, cell-cluster formation was confirmed depending on the concentration of the purified 70S ribosome fraction.

Figure 6:
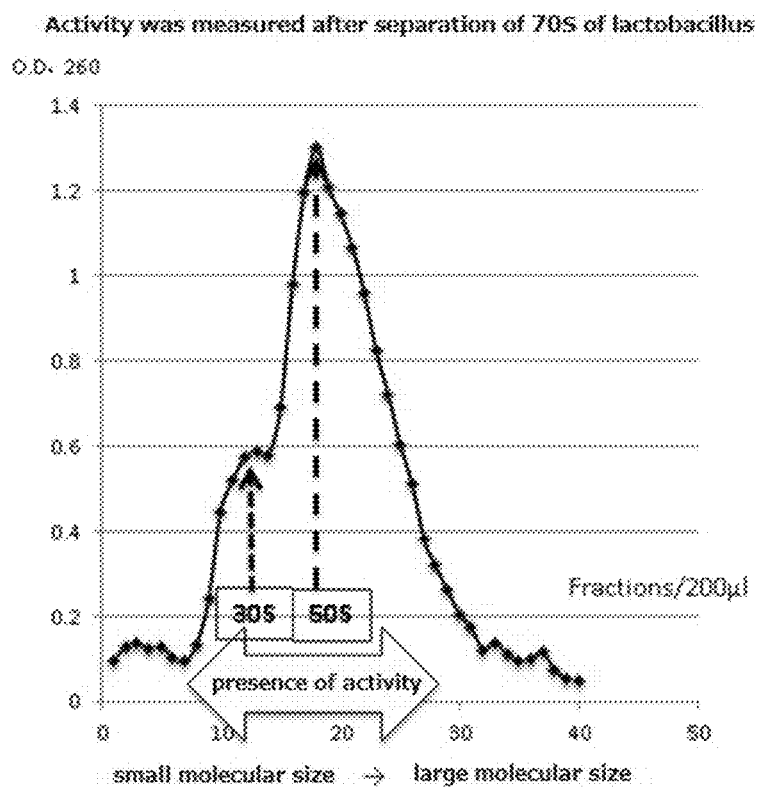
FIG. 6 is a view showing purification of a 50S ribosome and a 30S ribosome from a *Lactobacillus*-derived 70S ribosome fraction, and the cell-cluster forming ability of each fraction.

Example 8: The Cell-Cluster Forming Ability of a 30S Ribosome and a 50S Ribosome The 70S ribosome fraction which has been purified from *Lactobacillus* in Example 7 was further separated into a 30S ribosome fraction and a 50S ribosome fraction, and purified as follows:
(Reagent)
TMA-II buffer (10 mM Tris-HCl, pH 7.8, 30 mM $NH_4Cl$, 0.3 mM $MgCl_2$, 6 mM 2-mercaptoethanol)
Suc40-TMA-II (40% sucrose in TMA-II buffer)
Suc10-TMA-II (10% sucrose in TMA-II buffer)
(Preparation Step)
1) Dialysis: Using a TMA-II buffer, and a dialysis cassette (Thermo Slide-A-Lyzer dialysis cassette 20,000 MWCO 3 ml capacity), a 70S sample was dialyzed overnight.
2) Centrifugation
A centrifugation tube gradient was made as follows:
Rotor: Swing SW41 (maximum 13.2 ml)×6; Rmax=15.31 cm; tube: UC tube 344059 (purchased from GTC).
Into a UC tube was placed 5 ml of Suc40-TMA-II, and 5 ml of Suc10-TMA II was overlaid thereon. The tube was closed with plastic paraffin film (Parafilm®), and the tube was laid on its side, and allowed to stand at room temperature for 4 hours. The tube was slowly erected, and allowed to stand at 4° C. overnight.
50% sucrose (100 g sucrose/200 ml Milli-Q water) was prepared on that day.
The dialyzed sample (0.3 ml) was overlaid on the tube which had been prepared on the previous day. The sample was set in a SW41 rotor, and centrifuged at 35000 rpm and 4° C. for 3 hours (ac9 br0).
3) Fractionation with a fraction collector
A fraction collector for an Eppendorf tube was set up (200 μl/tube), the centrifuged tube was fixed, an upper portion was connected to the fraction connector, a 18G needle was pierced into a lower portion of the tube, 50% sucrose was placed therein with a peristaltic pump, and the sample which was pushed from an upper portion was recovered with the fraction collector. OD260/280 of the recovered sample was measured, and the concentration and the purity were examined.
(Result)
The result is shown in FIG. 6. A 30S ribosome fraction and a 50S ribosome fraction derived from *Lactobacillus* were purified.

Figure 7:
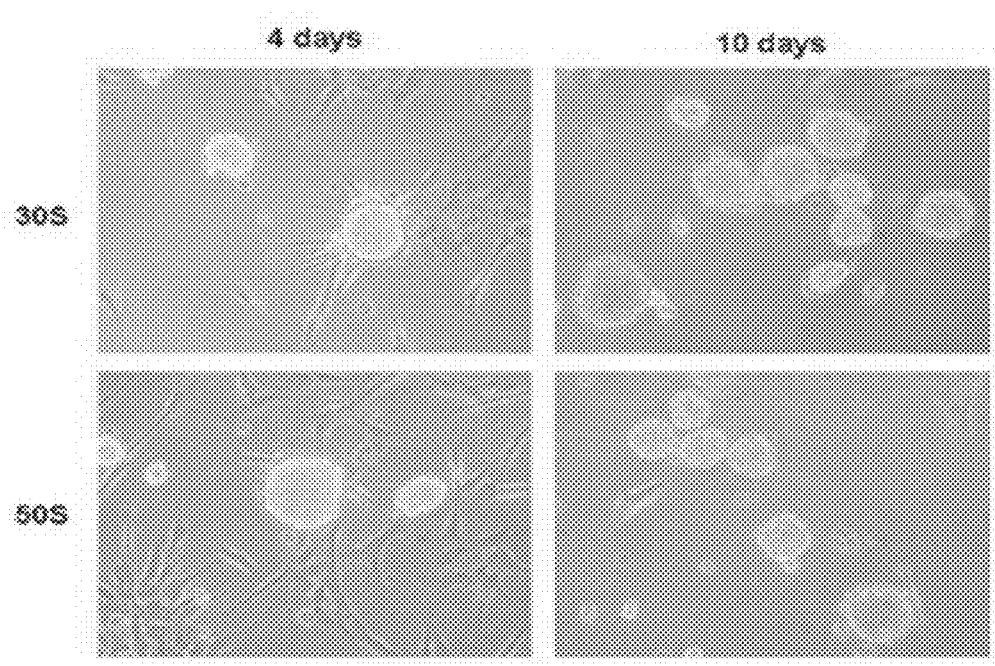
FIG. 7 shows the shape of HDF cells which were cultured with a *Lactobacillus*-derived 30S ribosome fraction or 50S ribosome fraction (4th day, 10th day).

Example 9: The Cell-Cluster Forming Ability of a Purified *Lactobacillus* 30S Ribosome Fraction and 50S Ribosome Fraction Using the purified *Lactobacillus* 30S ribosome fraction or 50S ribosome fraction, the cell-cluster forming ability was examined using HDF cells, as in Example 2.
The result is shown in FIG. 7. When either of the 30S ribosome fraction or the 50S ribosome fraction was used, a cell-cluster was formed.

Example 10: Induction of Differentiation from a Formed Cell-Cluster

Figure 8:
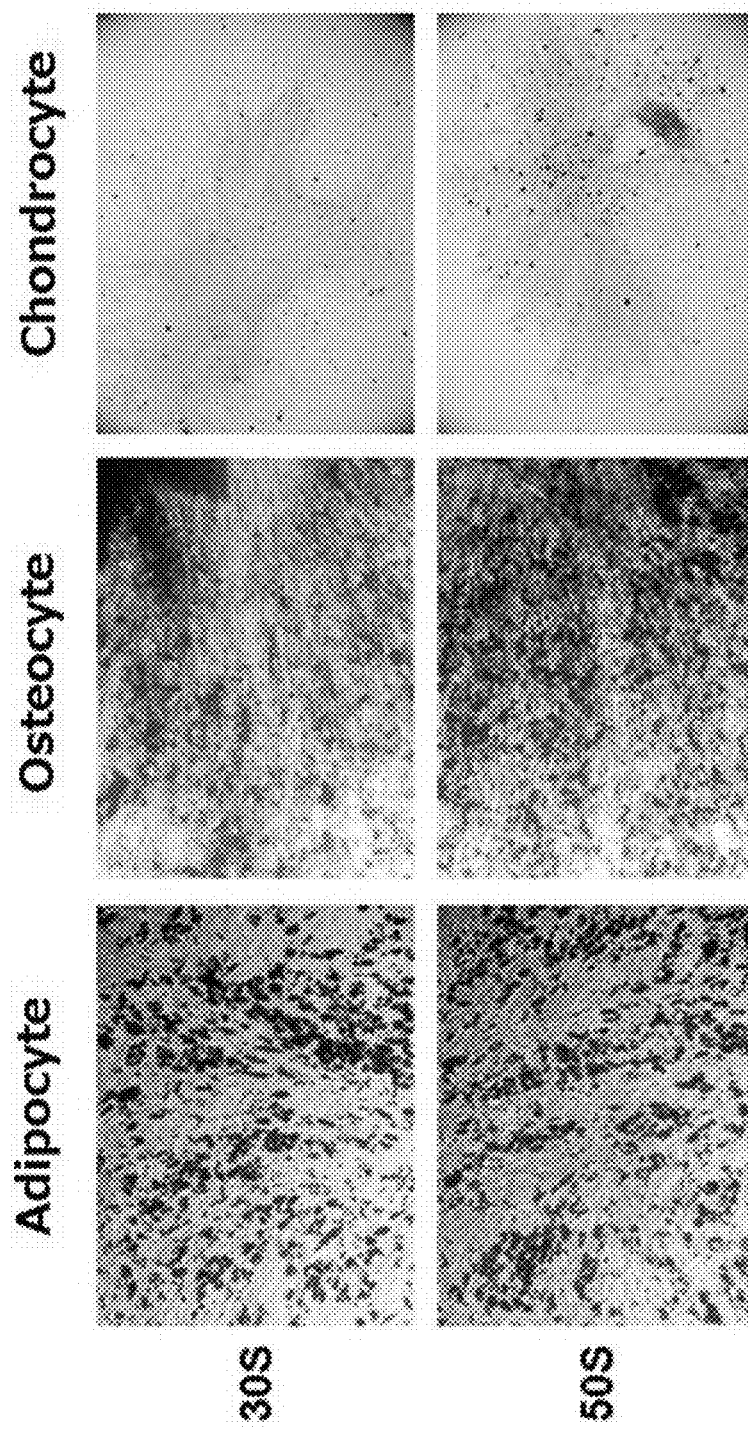
FIG. 8 shows the result of culturing of HDF cells treated with a *Lactobacillus*-derived 30S ribosome or 50S ribosome, in a medium which induces differentiation into an adipocyte, an osteocyte, or a chondorocyte, and subsequent Oil Red O staining (adipocyte), Alizarin Red S staining (osteocyte), or Alcian Blue staining (chondrocyte) of each cell.

HDF cells were treated with the 30S ribosome fraction or the 50S ribosome fraction derived from *Lactobacillus* (Lac), a cell-cluster was picked up after 2 weeks, the medium was exchanged with a culturing solution (GIBCO; A10072-01, A10070-01, A10071-01) which promotes induction of differentiation into an adipocyte, an osteocyte or a chondrocyte, and the cells were further cultured for 3 weeks (a half of a culturing solution was exchanged every 3 days).
The cells after culturing in each differentiation-inducing medium were stained with each cell marker. The result is shown in FIG. 8. The cell-cluster was stained by Oil Red O staining (adipocyte), Alizarin Red S staining (osteocyte), Alcian Blue staining (chondrocyte), and induction of differentiation into each cell could be confirmed.

Example 11: Influence of an Endocytosis Inhibitor on Cell-Cluster Formation

In the presence of an endocytosis inhibitor shown in the following Table, the cell-cluster forming ability was examined using the *Lactobacillus* 70S ribosome fraction prepared in Example 6. The 70S ribosome fraction was placed into a 96-well plate (0.5 μg/50 μl/well), HDF cells (20,000 cells/100 μl) were added, and each inhibitor (50 μl) was added. The cells were cultured in a $CO_2$ incubator for 2 days, and the number of the formed cell-clusters was measured. The inhibitor was used with the concentration shown in Table being the standard concentration (concentration "5" in FIG. 9). Accordingly, for example, in the case of CP, the concentration "5" is 10 μM, and the concentration "10" is 20 μM. In addition, the MTT assay (measurement of cell death by colorimetric method) was conducted.

| Inhibitor | Concentration | Effect of Inhibitor |
|---|---|---|
| Chlorpromazine (CP) | 10 μM | Inhibitor of clathrin-dependent endocytosis |
| Cytochalasin B (CC) | 2 μM | Inhibitor of actin polymerization |
| Filipin (FP) | 2 μg/ml | Inhibitor of caveolin-dependent endocytosis |
| Nystatin (NY) | 20 μM | Increases permeability of cell membrane of sensitive fungi by sterol binding |
| Methyl-β-cyclodextrin (MC) | 5 mM | Inhibitor of lipid raft synthesis and caveolin-dependent endocytosis |
| 5-(N-Ethyl-N-isopropyl)-amiloride (EA) | 25 μM | Selective blocker of Na+/H+ antiport |
| Bafilomycin A1 (BM) | 0.5 μM | Inhibitor of vacuolar H+-ATPase |
| Concanamycin A (CM) | 100 nM | Inhibitor of acidification of organelles and perforin-mediated cytotoxicity |
| Genistein (GS) | 200 μM | Inhibitor of caveolin-dependent endocytosis |

Figure 9:
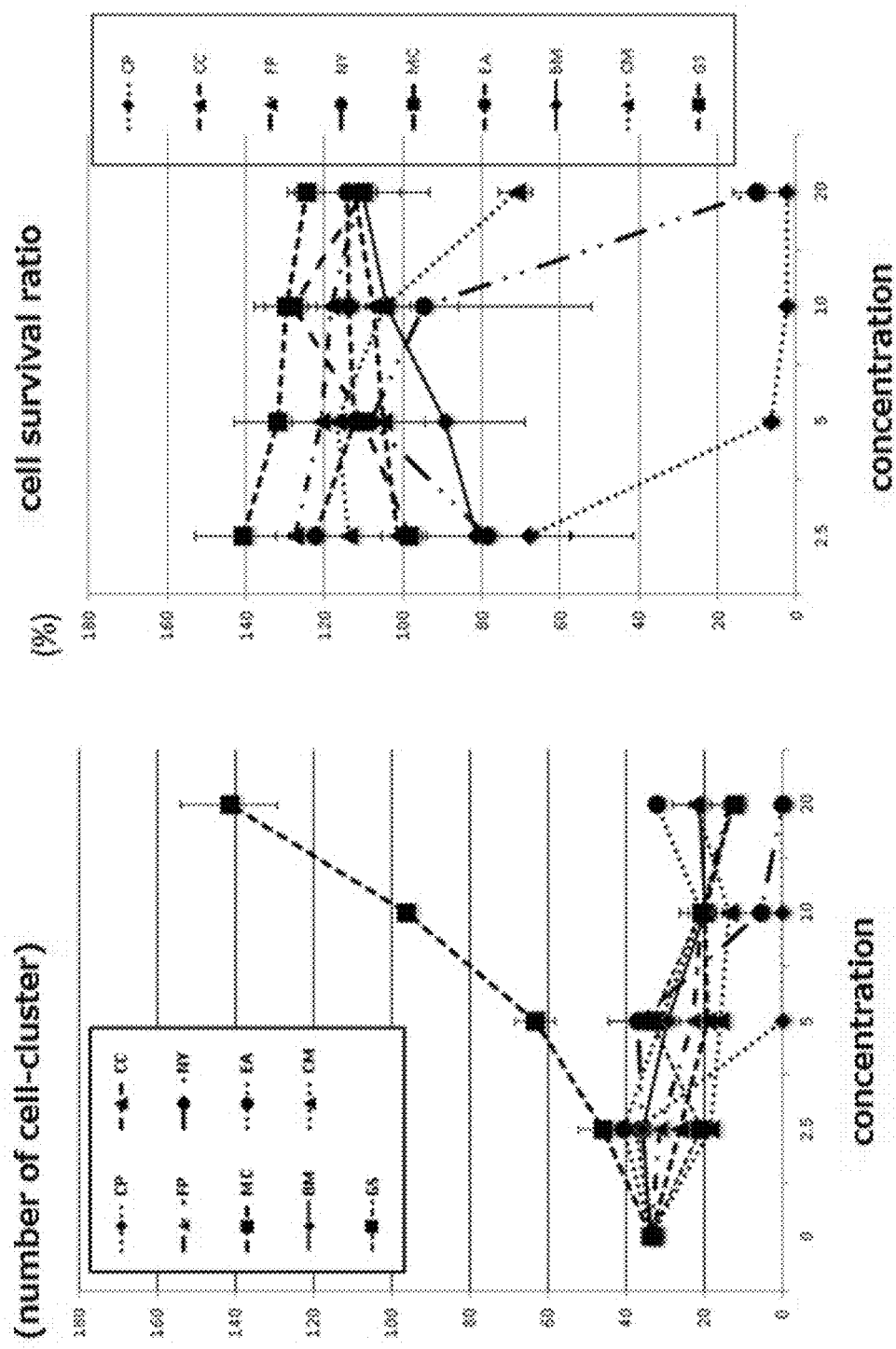
FIG. 9 is a view showing confirmation of influence of an endocytosis inhibitor on the cell-cluster forming ability of a *Lactobacillus*-derived 70S ribosome fraction. A left view shows observation of change in the number of cell-clusters, and a right view shows measurement of the cell survival ratio by the MTT assay. As the cell survival ratio, no inhibitor was let to be 100%.
Figure 10:
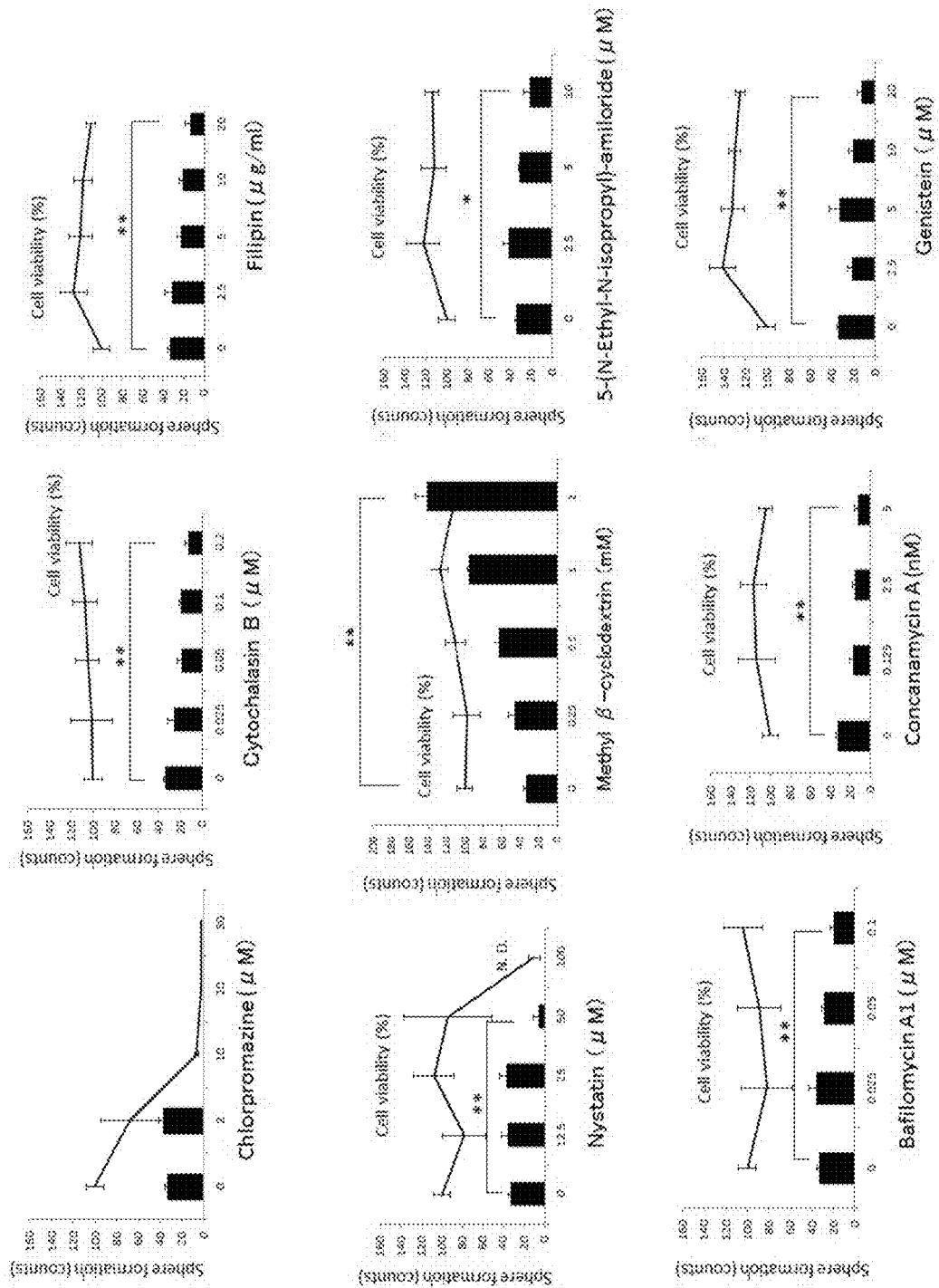
FIG. 10 is a view showing that the cell survival ratio and the cell-cluster forming ability being the result of FIG. 9 are re-plotted on the same graph, concerning each inhibitor. "*" shows 0.05 or less in the t test, and "**" shows 0.01 or less in the t test.

The results are shown in FIG. 9 and FIG. 10. In the presence of MC, the number of the cell-clusters was increased concentration-dependently. In addition, in the presence of CP and NY, the number of the cell-clusters was decreased, and it is considered that this is due to toxicity of these reagents. Regarding other inhibitors, since the number of the cell-clusters was unconditionally decreased, it is considered that endocytosis is involved in cell-cluster formation.

Example 12: Cell-Cluster Formation Using a Non-Enzymatic Cell Peeling Liquid

Figure 11:
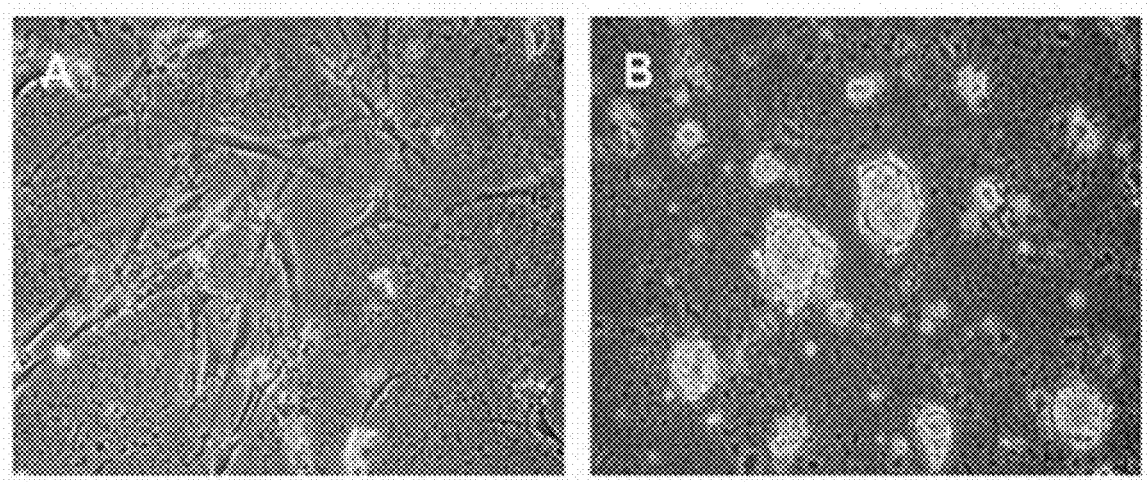
FIG. 11 shows the result of confirmation of cell-cluster formation from HDF cells which were peeled with a non-enzymatic cell peeling liquid from a dish, using a partially purified ribosome fraction. "A" shows cells which were cultured without a partially purified ribosome fraction, and "B" shows cells which were cultured in the presence of a partially purified ribosome fraction (after culturing for 3 days).

In order to examine a difference from Muse cells, cells were peeled from a dish using a non-enzymatic cell peeling liquid (Sigma, C1419) according to the manufacturer's protocol, and then, the same experiment as that of Example 2 was conducted using the partially purified ribosome fraction described in Example 6. The result is shown in FIG. 11. Even when the cells were peeled by a method not using trypsin, a cell-cluster was formed.

Examples 13: Endocytosis Activity by Trypsin Treatment

There is a report that the endocytosis activity is increased by trypsin treatment, but there is no report that this is confirmed by HDF, and a method of increasing the endocytosis activity by trypsin treatment and taking a macromolecule into cells has not been reported, unlike electroporation and transfection which are generally known. Then, whether the uptake activity of cells is actually increased by HDF or not was tested using labelled nanolatex particles having approximately the same size as that of a ribosome. Fluoresbrite Carboxylate Microspheres (2.5% Solids-Latex), and 0.05 μm YG (Polysciences, Inc.) were used. In place of a ribosome solution, 1 μl of labelled nanolatex particles were added. After incubation was performed overnight to adhere the cells, a surface was washed with PBS, and observed. As a result, in the cells which were trypsin-treated, uptake of Microspheres was observed, and those having a size close to a size of a ribosome (20 nM) were taken in, but in untreated cells, only slight uptake was observed. Thereby, it was found out that the endocytosis activity was increased by trypsin treatment.

Example 14: Treatment by Transfection

Figure 12:
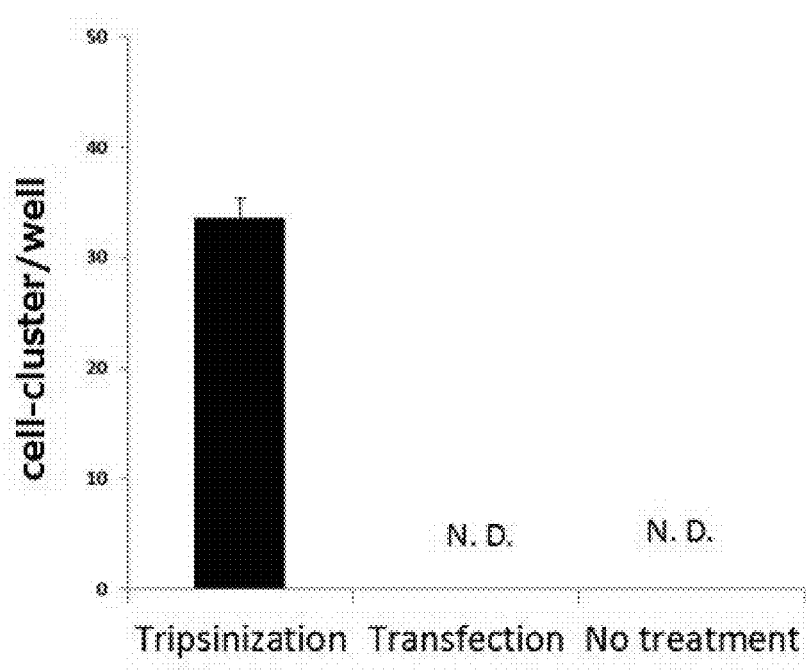
FIG. 12 shows the result of confirmation of cell-cluster formation by transfection.

Whether the same effect as that of trypsin treatment can be reproduced by transfection or not was studied using LipofectAMINE2000 (Invitrogen). The method was performed as in Example 2, and was implemented according to the manufacturer's protocol. As a ribosome, the purified 70S ribosome fraction of Lac was used, and the fraction was added so that a ribosome became 1 μg ribosome/2×10$^4$ cells/well. The result is shown in FIG. 12. It was found out that, by transfection, formation of a cell-cluster does not occur.

Example 15: The Cell-Cluster Forming Ability of Ribosome Fractions Derived from a Mammal A partially purified ribosome fraction (fraction before gradient ultracentrifugation treatment) and a 80S ribosome fraction were purified from rat small intestine cells (IEC-6) according to Anger et al. (Nature 2013, p. 80, vol. 497), and the cell-cluster forming ability was examined using HDF cells as in Example 2. The result is shown in FIG. 13. A cell-cluster was formed by the partially purified ribosome fraction and the 80S ribosome fraction derived from a mammal.

Figure 15:
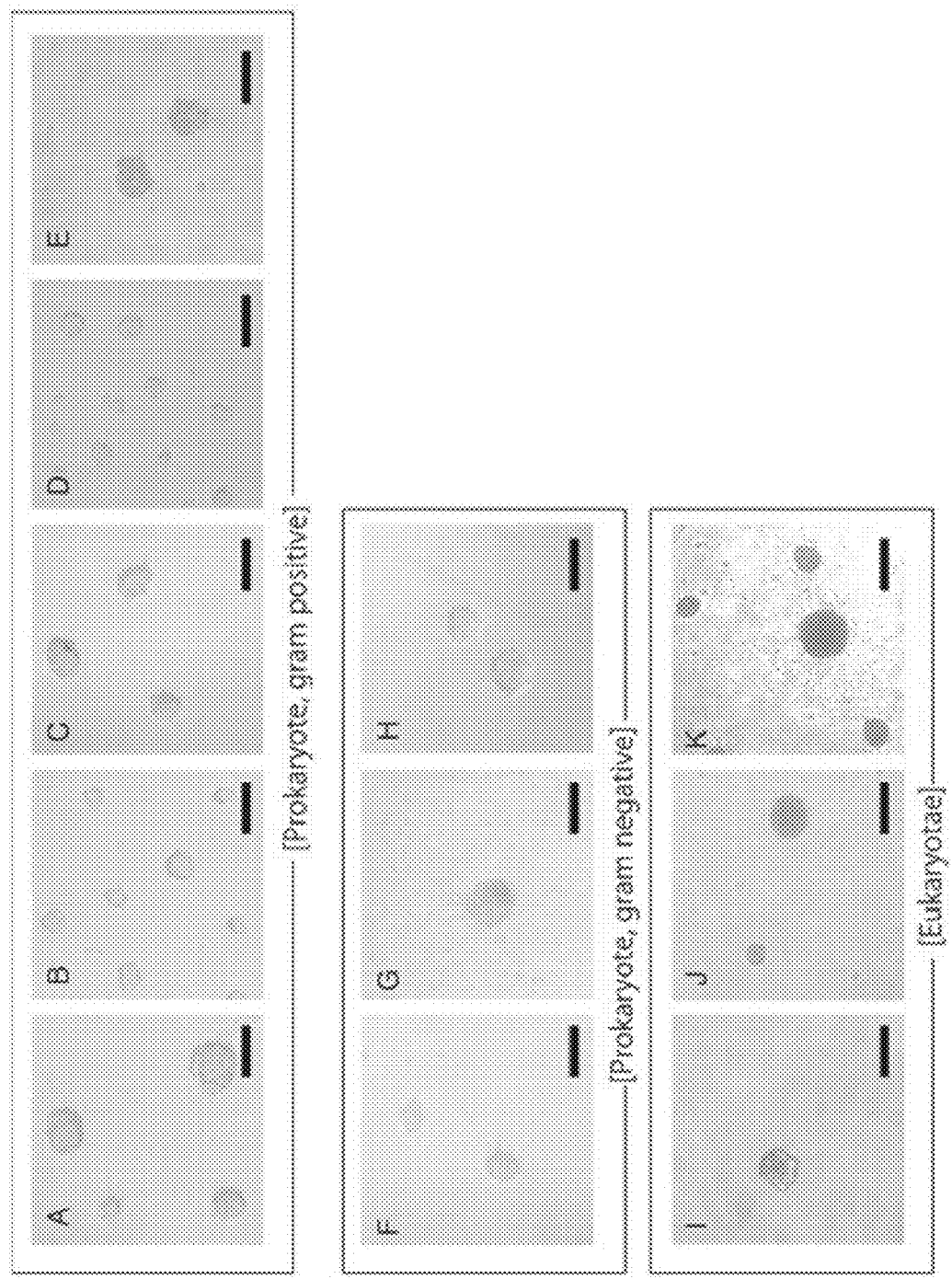
FIG. 15 is a photograph of a cell-cluster which was formed by addition of purified ribosome fractions (A-H: purified 70S; I-K: purified 80S), from various bacteria or cells. (A) *Lactobacillus acidophilus* JCM 1021, (B) *Lactobacillus reuteri* JCM 1112, (C) *Lactobacillus casei* JCM1134, (D) *Bacillus subtilis* subsp. 168 JCM10629, (E) *Staphylococcus epidermidis* JCM2414, (F) *Pseudomonas putida* JCM 13063, (G) *Mesorhizobium loti* JCM 21590, (H) *Escherichia coli* JE28, (I) *Saccharomyces cerevisiae* BY20118, (J) *Rattus norvegicus* IEC-6, (K) Homo sapience dermal fibroblast. Bar indicates 0.1 mm.

Example 16: The Cell-Cluster Forming Ability of Ribosome Fractions Derived from Other Organisms From bacteria and cells shown in FIG. 14, a partially purified ribosome fraction and a 70S ribosome fraction or a 80S ribosome fraction were purified, and the cell-cluster forming ability was examined using HDF cells, as in Example 2. Purification of a ribosome fraction from a prokaryote was carried out according to Example 6, and purification of a ribosome fraction from a eukaryote was carried out according to the description of the report of Anger et al. (aforementioned). Each abbreviation in the figure indicates the following bacteria or cells; Lac: *Lactobacillus acidophilus* JCM 1021, Lca: *Lactobacillus casei* JCM1134, Lre: *Lactobacillus reuteri* JCM 1112, Sep: *Staphylococcus epidermidis* JCM2414, Bsu: *Bacillus subtilis* subsp. 168 JCM10629, Eco: *Escherichia coli* JE28, Ppu: *Pseudomonas putida* JCM 13063, Mlo: *Mesorhizobium loti* JCM 21590, Sce: Saccharomyces cerevisiae BY20118, IEC-6: Rattus norvegicus IEC-6. The result is shown in FIG. 14. A cell-cluster was formed by ribosome fractions derived from examined all cell species. Additionally, when the cell-cluster forming ability was similarly confirmed using a ribosome fraction purified from HDF, formation of a cell-cluster could be similarly confirmed. The result of formation of each cell-cluster is shown in FIG. 15.

Example 17: The Cell-Cluster Forming Ability of a Ribosome Fraction on Floating Cells In order to examine the effect on floating cells, as in Example 6, a partially purified ribosome fraction was prepared from *Lactobacillus* (Lac), and the cell-cluster forming ability was examined using trypsin-treated mouse lymphocyte (WEHI, Ba/F3).

Figure 16:
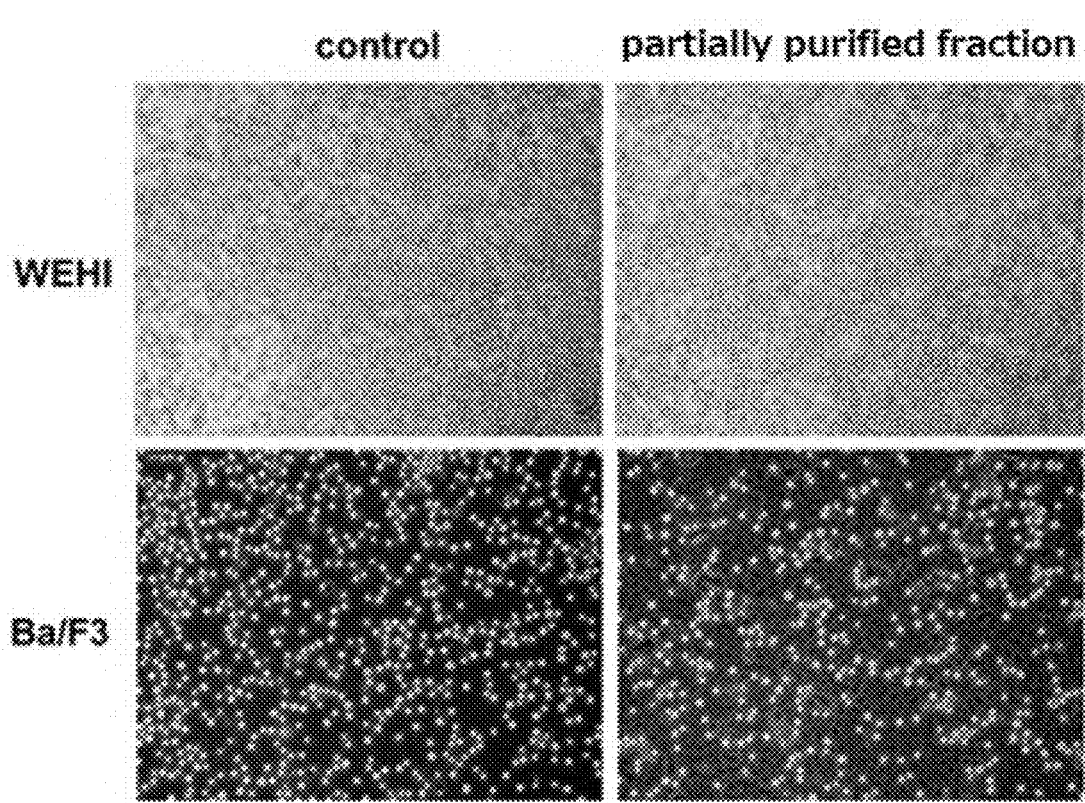
FIG. 16 shows the result of confirmation of the cell-cluster forming ability of a partially purified ribosome fraction using floating cells (mouse lymphocyte: WEHI and Ba/F3). "A" shows cells which were cultured without a partially purified ribosome fraction, and "B" shows cells which were cultured in the presence of a partially purified ribosome fraction (after culturing for 4 days).

As shown in FIG. 16, a cell-cluster was not formed.

Example 18: Confirmation of a Pluripotent Marker in Formed Cell-Cluster Cells

Using a 70S ribosome fraction of *Lactobacillus* (Lac), a cell-cluster was formed, and alkaline phosphatase staining was performed on 3rd day (A), on 7th day (B) and on 10th day (C). Using BM purple (manufactured by Roche) as the alkaline phosphatase, measurement was performed according to the manufacturer's protocol. As a result, a cell-cluster continuously exhibited the alkaline phosphatase activity from 3rd day.

Then, a cell-cluster was formed using a *Lactobacillus* 70S ribosome fraction, as in Example 2. After culturing for 2 weeks, the cell-cluster was stained according to the manufacturer's protocol, using a mouse anti-α-Nanog antibody (ReproCELL), a rat anti-Oct3/4 antibody (R & D), a mouse anti-TRA-1-60 antibody (Life Technologies), a mouse anti-SSEA4 antibody (Life Technologies), and a rat anti-Sox2 antibody (Life Technologies). As a result, the cell-cluster was stained with antibodies recognizing Nanog, Oct3/4, TRA-1-60, SSEA4, and Sox2. In addition, using the cell-clusters on 1st day and 20th day of culturing, the TUNEL assay was performed to examine cell death. As a result, in the cell-clusters after culturing for one day and for 20 days, cell death was not observed.

Example 19: Influence of Heat Treatment of a Ribosome

Figure 17:
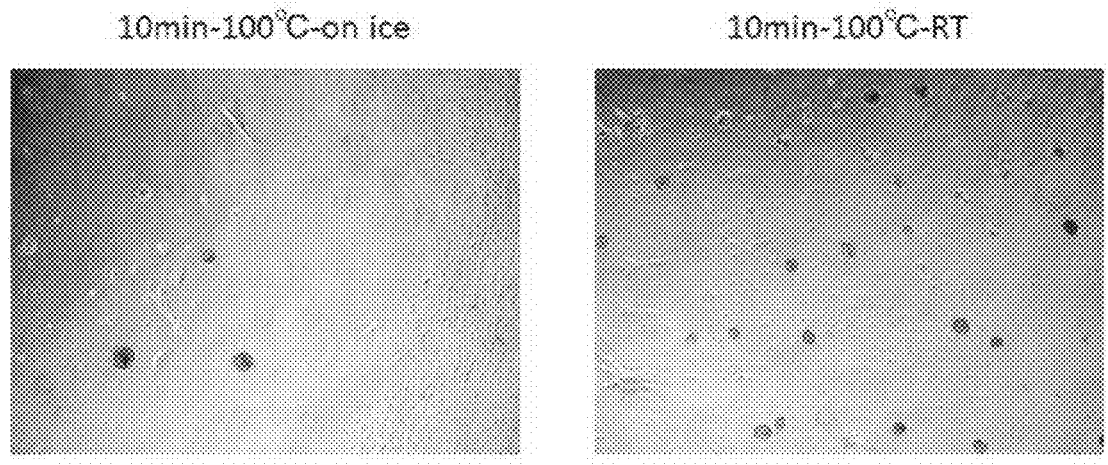
FIG. 17 shows the result of confirmation of influence of heat treatment on a purified ribosome fraction. A left view is the result of use of a ribosome fraction which was placed on an ice immediately after heating at 100 degree for 10 minutes, and a right view is the result of use of a ribosome fraction which was allowed to stand at room temperature for 10 minutes, after cooling to room temperature immediately after heating at 100 degree for 10 minutes.

Cell-cluster forming ability was examined using HDF cells, as in Example 2, in each of the case where immediately after a purified *Lactobacillus* 70S ribosome fraction was heated at 100 degree for 10 minutes, the fraction was placed on an ice, and the case where immediately after a purified *Lactobacillus* 70S ribosome fraction was heated at 100 degree for 10 minutes, the fraction was allowed to stand at room temperature. The result is shown in FIG. 17. When the fraction was allowed to stand at room temperature for 10 minutes, a cell-cluster was formed, but when the fraction was placed on an ice immediately after heating, the cell-cluster forming ability was decreased. Thereby, it was found out that a high order structure of a RNA contributes to the cell-cluster forming ability.

Example 20: Induction of Differentiation from Formed Cell-Cluster Cells into a Nerve Cell A 70S ribosome fraction was prepared from *Lactobacillus* (Lac), and as in Example 2, a cell-cluster was formed. After culturing for 2 weeks, induction and differentiation of a nerve cell were performed using the Human ES/iPS Neurogenesis Kit (Millipore), and an immunostaining with a mouse-anti α-Tuj1 antibody, a rat anti-neurofilament antibody, or a mouse anti-MAP2 antibody was performed. As a result, cells of a part of the cell-cluster were recognized by three nerve cell marker antibodies. From this, differentiation from the induced cell-cluster into a nerve cell was observed.

Example 21: Induction of Differentiation from Formed Cell-Cluster Cells into a Cardiac Muscle Cell A 70S ribosome fraction was prepared from *Lactobacillus* (Lac), and as in Example 2, a cell-cluster was formed. After culturing for 2 weeks, induction and differentiation of a cardiac muscle cell were performed using the Cardiomyocyte Differentiation Kit (Millipore), and an immunostaining with a rabbit anti-α-NKX2 antibody and a mouse anti-TNNT2 antibody was performed. As a result, cells of a part of the cell-cluster were recognized by two cardiac muscle cell marker antibodies. From this, differentiation into a cardiac muscle cell was observed.

Example 22: Confirmation of Epithelial-Mesenchymal Transition

HDF cells were subjected to an immunostaining using a rabbit anti-α-Snail antibody (Abcam) and a mouse anti-α-Twist antibody (Abcam).
A 70S ribosome fraction was prepared from *Lactobacillus* (Lac), and as in Example 2, a cell-cluster was formed. After culturing for two weeks, the cell-cluster was subjected to immunostaining using a rabbit anti-α-Snail antibody, a mouse anti-α-Twist antibody, and a mouse anti-α-E Cadherin (Abcam) antibody.
As a result, HDF cells were stained with an anti-α-Snail antibody and an anti-α-Twist antibody little, but the cells which had form the cell-cluster were recognized with these antibodies. In addition, the cells which had formed the cell-cluster were not stained with an anti-α-E Cadherin antibody. These results show that the formed cell-cluster caused epithelial-mesenchymal transition.

Example 23: Application to a Cancer Cell

A 70S ribosome fraction was prepared from *Lactobacillus* (Lac), a lung cancer cell strain (A549; RBRC-RCB0098), a liver cancer cell strain (HepG2; RBRC-RCB1648), and a breast cancer cell strain (MCF7; RBRC-RCB1904) were obtained from Institute of Physical and Chemical Research (RIKEN), BioResource Center, and the same experiment as that of Example 2 was performed to form a cell-cluster. Thereafter, the cell-cluster was cultured for 2 weeks, the medium was exchanged with a culturing liquid (GIBCO: A10070-01, A10072-01) which promotes induction of differentiation into an adipocyte and an osteocyte, and the cells were further cultured for 2 to 3 weeks.

Figure 18:
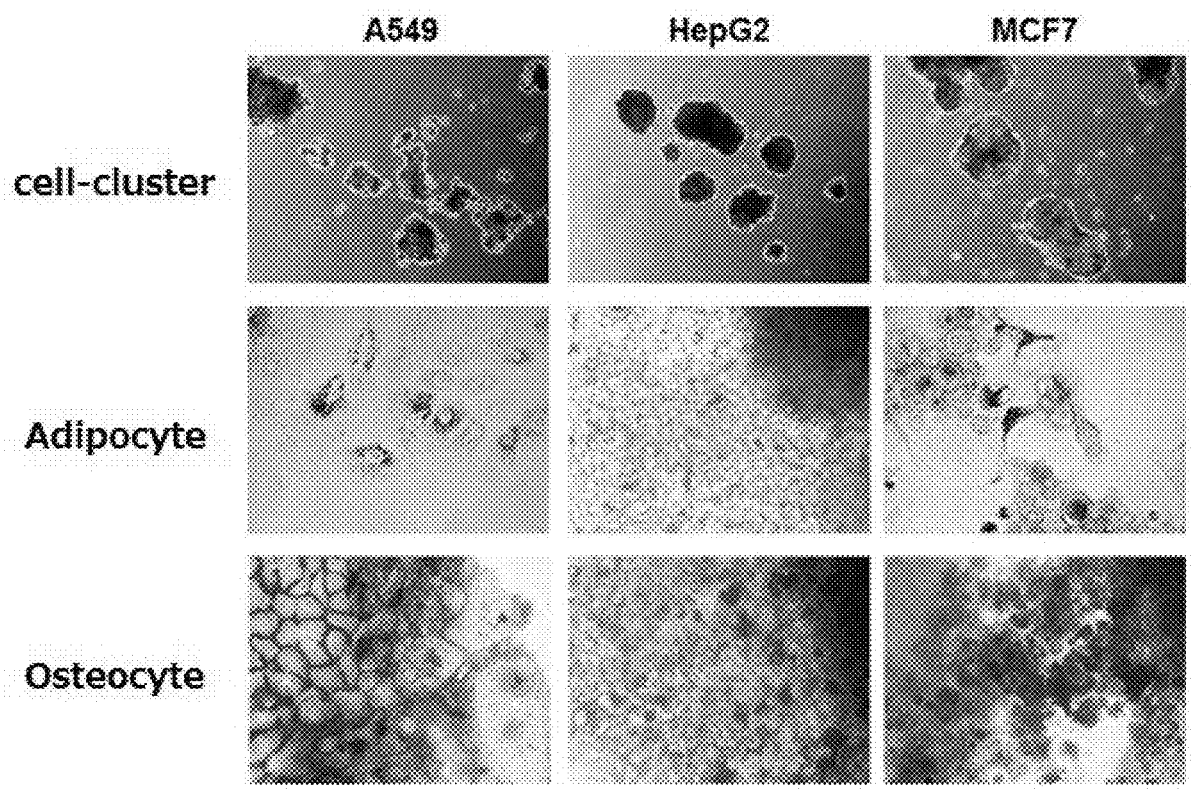
FIG. 18 shows the result of Oil Red O staining (adipocyte), or Alcian Blue staining (chondrocyte) of each cell, after culturing of a cell-cluster which was formed by treating various cancer cells (A549, HepG2, MCF7) with a *Lactobacillus* 70S ribosome fraction, in a medium which induces differentiation into a adipocyte or a osteocyte.

The result is shown in FIG. 18. As shown in the figure, it was confirmed that the lung cancer cell, the liver cancer cell, and the breast cancer cell were reprogrammed by uptake of the *Lactobacillus*-derived 70S ribosome fraction, stained by Oil Red O staining (adipocyte), and Alizarin Red S staining (osteocyte), and differentiated into an adipocyte and an osteocyte.

Example 24: Genome DNA Analysis of a Formed Cell-Cluster

Using a cell-cluster after 16 days from uptake of a *Lactobacillus* (Lac)-derived 70S ribosome fraction into HDF cells, chromosome structure analysis by CytoScan was performed. In a normal pluripotent stem cell, karyotype analysis by Q-band or G-band observation is general, but these cells do not proliferate, a chromosome having an opened structure cannot be observed. Accordingly, CytoScan (one of microarrays; A genome DNA is detected by hybridizing it with chips comprehensively covering necessary genes for seeing a chromosomal structure, such as SNP marker etc.) analysis was performed.
A genome DNA was extracted from the cell-cluster and purified with the Qiagen DNeasy blood & tissue kit. A purified genome DNA was sent to Support Center for Advanced Medical Sciences, Institute of Medical Sciences, Tokushima University Graduate School, and analysis was performed. In analysis, after quality of a genome DNA was checked, a microarray reaction and detection were performed.
As a result, a trisomy was detected in chromosomes 14 and 17, but since the trisomy in 14 necessarily appears based on the algorism, only 17 was confirmed as the trisomy. Since the pluripotent cell which was prepared this time is not a single cell clone, but an aggregate, there is a possibility that the trisomy is generated as the whole population. Three copies of a q21.31 region of a chromosome 17 exist, but in this region, the trisomy occurs relatively frequently at establishment of the ES cell, thus, this is not particularly problematic.
The foregoing merely illustrates objects and subjects of the present invention, and does not limit the accompanying Claims. Without departing from the accompanying Claims, various modifications and alterations to the described embodiments will be apparent to those skilled in the art in view of the teachings herein.

INDUSTRIAL APPLICABILITY

The present invention is useful as a method for inducing reprogramming of a somatic cell, and further, as a method for producing a pluripotent cell from a somatic cell. Further, the method for producing a pluripotent cell according to the present invention is useful for the medicine field (drug development research, as well as study of safety, efficiency and side effect of medicaments), disease research (elucidation of cause for an intractable disease, development of a treating method and a preventing method for such disease), regenerative medicine (repair of the function of nerve, blood vessel, organ), as well as the food field.

What is claimed is:
1. A method for inducing reprogramming of a cell that is an isolated somatic cell or cancer cell of a mammal, comprising
   a) culturing the cell with a reprogramming agent, wherein the agent is a 70S, 50S or 30S ribosome subunit derived from a prokaryote, b) forming a ribosome-induced pluripotent cell cluster, and c) recovering the ribosome-induced cell-cluster, wherein the cell-cluster expresses Nanog, Oct3/4, TRA-1-60, SSEA4, and Sox 2, and wherein the somatic cell is a human fibroblast cell, and the cancer cell is selected from the group consisting of human breast cancer cells, human liver cancer cells, and human lung cancer cells, and wherein the reprogramming transforms the somatic cell or the cancer cell into a pluripotent cell, wherein the cell is an adherent cell, wherein the method further comprises a step of culturing or maintaining the adherent cell on a cell support and peeling the adherent cell from the cell support, followed by the step of culturing the cell with the reprogramming agent, and wherein the step of peeling the cell is performed by trypsin treatment.

2. The method according to claim 1, wherein the culture of the cell with the reprogramming agent is performed in the presence of methyl-β-cyclodextrin.

3. The method according to claim 1, wherein the agent is a purified ribosome subunit.

4. The method according to claim 3, wherein the ribosome subunit is a purified 70 S ribosome subunit.

5. The method according to claim 1, wherein the prokaryote is selected from the group consisting of *Lactobacillus acidophilus*, *Lactobacillus casei*, *Lactobacillus reuteri*, *Staphylococcus epidermidis*, *Bacillus subtilis*, *Escherichia coli*, and *Pseudomonas putida*.

6. The method according to claim 1, wherein the agent is a 70S subunit.

7. The method according to claim 1, wherein the agent is a 30S subunit.

8. The method according to claim 1, wherein the agent is a 50S subunit.

9. The method of claim 1, comprising forming the cell-cluster expressing Nanog, Oct3/4, TRA-1-60, SSEA4 and Sox2 and the cell cluster contains cells which can be differentiated into neural cells expressing Tuj1+Neurofilament+MAP2+or cardiac muscle cells expressing alpha-NKX2+TNNT2+.

* * * * *